United States Patent
Kato et al.

(10) Patent No.: US 8,760,155 B2
(45) Date of Patent: Jun. 24, 2014

(54) MAGNETISM MEASURING METHOD AND DEVICE

(75) Inventors: Hiroharu Kato, Tokyo (JP); Akio Nagamune, Tokyo (JP); Toshito Takamiya, Tokyo (JP)

(73) Assignee: JFE Steel Corporation (JP)

( * ) Notice: Subject to any disclaimer, the term of this patent is extended or adjusted under 35 U.S.C. 154(b) by 567 days.

(21) Appl. No.: 13/059,467

(22) PCT Filed: Aug. 26, 2009

(86) PCT No.: PCT/JP2009/065284
§ 371 (c)(1),
(2), (4) Date: Feb. 17, 2011

(87) PCT Pub. No.: WO2010/024454
PCT Pub. Date: Mar. 4, 2010

(65) Prior Publication Data
US 2011/0148405 A1    Jun. 23, 2011

(30) Foreign Application Priority Data

Aug. 27, 2008  (JP) ................................. 2008-217477

(51) Int. Cl.
*G01N 27/72*    (2006.01)

(52) U.S. Cl.
USPC .......................................... 324/228; 324/239

(58) Field of Classification Search
USPC ................................. 324/239, 228
See application file for complete search history.

(56) References Cited

U.S. PATENT DOCUMENTS

| 5,266,129 A | 11/1993 | Minakuchi et al. | |
|---|---|---|---|
| 2003/0188806 A1* | 10/2003 | Fujii et al. | 148/112 |
| 2005/0247374 A1* | 11/2005 | Choi et al. | 148/111 |

FOREIGN PATENT DOCUMENTS

| JP | 53-020986 A | 2/1978 |
|---|---|---|
| JP | 55-046143 A | 3/1980 |
| JP | 3-128850 | 12/1991 |
| JP | 8-036038 A | 2/1996 |
| JP | 2519615 B2 | 7/1996 |
| JP | 9-274017 A | 10/1997 |
| JP | 09274017 A * | 10/1997 |
| JP | 2001-228120 A | 8/2001 |
| JP | 2001228120 A * | 8/2001 |

OTHER PUBLICATIONS

Partial English Translation of JP 09274017 A, Oct. 21, 1997.*
Partial English Translation of JP 2001228120 A, Aug. 24, 2001.*
Japanese Industrial Standard, JIS C 2550: 2000, "Test Methods for Magnetic Steel Sheet and Strip," paragraph d) magmetization characteristics of 3 Definitions and symbols, pp. 2-3.
"Magnetic Material Reader," edited by Motohumi Homma and Akira Higuchi, *Kabushiki Gaisha, Kogyo Cyosakai*, 1998, pp. 41 and 42 (only English translation—4 pages).

* cited by examiner

*Primary Examiner* — Bot Ledynh
(74) *Attorney, Agent, or Firm* — DLA Piper LLP (US)

(57) ABSTRACT

A magnetism measuring method includes magnetizing a magnetic material with a direct current to a rotational magnetization region, performing an alternate current excitation in a direction having a component orthogonal to a direction of the direct current magnetization, and measuring a component of an alternate current magnetic field generated by an interaction with the magnetic material in a direction orthogonal to the direction of the direct current magnetization.

15 Claims, 8 Drawing Sheets

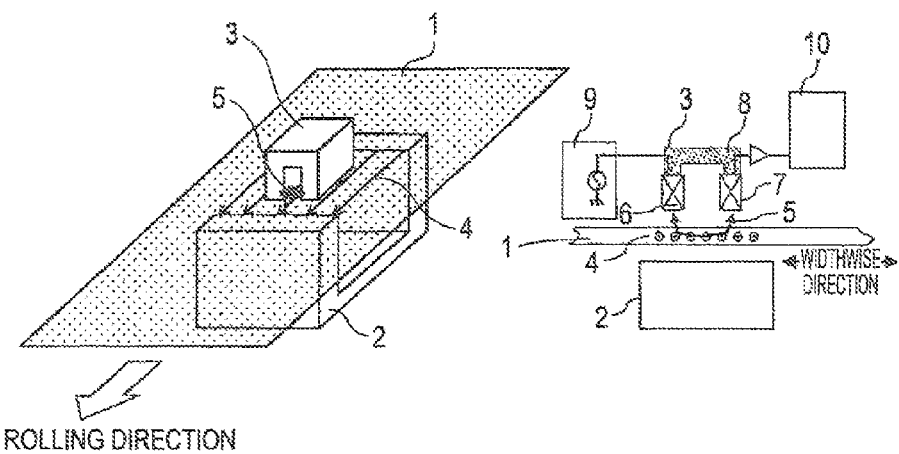
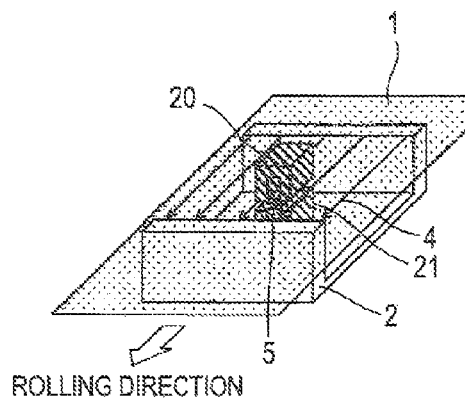
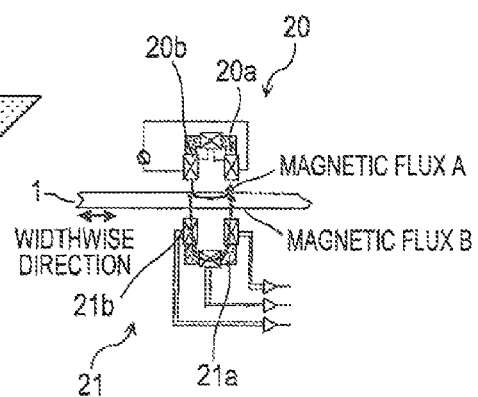

FIG.8A
FIG.8B
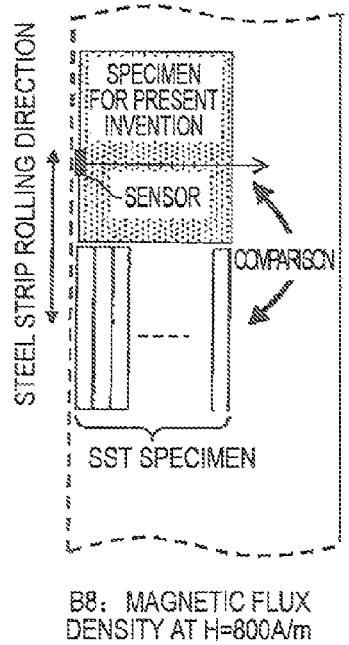
B8: MAGNETIC FLUX
DENSITY AT H=800A/m
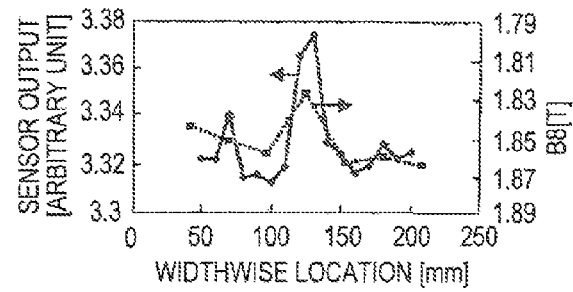
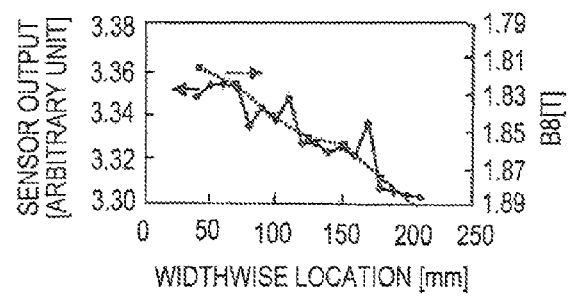

MAGNETISM MEASURING METHOD AND DEVICE

RELATED APPLICATIONS

This is a §371 of International Application No. PCT/JP2009/065284, with an international filing date of Aug. 26, 2009 (WO 2010/024454 A1, published Mar. 4, 2010), which is based on Japanese Patent Application No. 2008-217477, filed Aug. 27, 2008, the subject matter of which is incorporated by reference.

TECHNICAL FIELD

This disclosure relates to a magnetism measuring method and device which measure local magnetic properties of a magnetic material with high precision.

BACKGROUND

The non-contact measurement of electromagnetic properties of a metal material such as magnetic permeability, core loss and electric conductivity or a quantity of the metal material which has correlation to electromagnetic properties is used for various purposes. For example, in paragraph [0015] of Japanese Patent 2519615, there is the description on an example where iron loss is measured by a known method in such a manner that a primary coil and a secondary coil for measuring core loss are arranged in a manufacturing line of a grain-oriented electrical steel sheet (between an annealing furnace and an annealing separator coating device or during a period in which the annealing separator is applied by coating, is dried and is wound into a coil shape), and a steel sheet is made to pass through these coils. It is thought that, in this method, large-sized coils are used and an average core loss in the widthwise direction of the steel sheet is measured using an alternate current magnetic flux.

Further, in JP-A-53-20986, there is the description where an alternate current magnetic flux is applied to an object to be measured (an electric conductive object such as iron slab or hot rolled strip), and a change in electric conductivity and a change in magnetic permeability depending on a temperature of an object to be measured are measured by measuring a magnetic field which is generated by an interaction between the magnetic flux and the object to be measured, and the temperature of the object to be measured is measured eventually.

As sensors which serve for such measurement, sensors of various configurations are conceivable. Among these sensors, a sensor having a U-shaped core is one kind of general use sensor. For example, JP-A-8-36038 discloses an example of such a sensor for measuring magnetic permeability.

A method which evaluates magnetic property or the like by detecting an orientation of crystal grains, for example, using ultrasonic waves instead of detecting magnetic property per se is also considered as a non-contact means (although water is interposed).

However, the above-mentioned prior art has a drawback that local magnetic property within a range from several mm to several 10 mm cannot be measured with high precision while minimally being influenced by disturbances or the like.

The usual magnetic property measurement is generally performed in a domain wall motion region (or domain wall displacement region) where the difference in property between a sound portion which has achieved desired magnetic property and an unsound portion which has not yet achieved the desired magnetic property is extremely large. In the domain wall motion region, the magnetic property is also strongly influenced by factors such as a particle diameter, precipitates, stress (tension) which possibly become error factors. Further, the magnetic property is largely influenced by a plate edge (the plate edge being a portion where the property of a ferromagnetic material and the property of a non-magnetic material (air) are discontinuous thus forming a dead zone at an edge) or a change in liftoff (distance between the sensor and an object to be measured).

This is because, in the domain wall motion region, the differential magnetic permeability is large and a change in the differential magnetic permeability attributed to the fluctuation of measuring conditions is also large. Hence, a sensor output is largely changed due to the presence or the non-presence of the object to be measured (influence exerted by the plate edge) and a distance between the sensor and the object to be measured (influence of the change in liftoff). Under such circumstances, it has been difficult to realize the measurement with high precision, particularly, the stable measurement in on-line (in a manufacture line).

The method which uses ultrasonic waves may be influenced by a trivial change in shape of a steel sheet. Hence, the improvement of the precision of measurement is also desired.

It could therefore be helpful to provide a magnetism measuring method and device which can measure the local magnetic property of a magnetic material with high precision while being minimally influenced by disturbances or the like.

SUMMARY

We thus provide:
(1) A magnetism measuring method in which a magnetic material is magnetized with a direct current to a rotational magnetization region and an alternate current excitation is performed in a direction having a component orthogonal to a direction of the direct current magnetization, and a component of an alternate current magnetic field which is generated by an interaction with the magnetic material in a direction orthogonal to the direction of the direct current magnetization is measured.

That is, the magnetism measuring method is characterized in that the direct current magnetism is applied to the magnetic material thus magnetizing the magnetic material with a direct current to the rotational magnetization region, the alternate current magnetism is applied to the magnetic material thus performing the alternate current excitation in the direction that the direct current magnetization is oscillated, and the alternate current magnetic field generated by the interaction between the magnetic material and both of the direct current magnetism and the alternate current magnetism, particularly the component of the alternate current magnetic field in the alternate current excitation direction are measured.

(2) In the magnetism measuring method described in (1), the component of the alternate current magnetic field orthogonal to the direction of the direct current magnetization is measured on a side opposite to a side where the alternate current excitation is performed with the magnetic material sandwiched therebetween.

In the magnetism measuring method according to (2), it is desirable that the magnetic material has a sheet shape and the alternate current excitation is performed on one surface side of the magnetic material and the measurement of the component is performed on the other surface side of the magnetic material.

(3) In the magnetism measuring method described in (1), the alternate current excitation is performed at opposing positions on both sides which face each other with the magnetic material sandwiched between the opposing positions, and the component of the alternate current magnetic field in the direction orthogonal to the direction of the direct current magnetization is measured at both opposing positions respectively with an object to be measured sandwiched between the both opposition positions.

In the magnetism measuring method according to (3), it is desirable that the magnetic material has a sheet shape and the alternate current excitation and the measurement of the component are performed on both surface sides of the magnetic material.

(4) In the magnetism measuring method described in any one of (1) to (3), the magnetic material is a grain-oriented electrical steel sheet, and the direction of direct current magnetization is a rolling direction.

The rolling direction indicates a rolling direction when a steel sheet is formed by rolling (particularly cold rolling) a steel ingot (such as a slab) which constitutes a raw material of the grain-oriented electrical steel sheet.

(5) A magnetism measuring device which includes:
a direct current magnetizer which magnetizes a magnetic material with a direct current to a rotational magnetization region; and
a magnetic sensor which performs the alternate current excitation in a direction having a component orthogonal to a direction of the direct current magnetization, and measures the component of an alternate current magnetic field which is generated by an interaction with the magnetic material in the direction orthogonal to the direction of the direct current magnetization.

That is, the magnetism measuring device is characterized by including the direct current magnetizer which applies the direct current magnetism to the magnetic material thus magnetizing the magnetic material with a direct current to the rotational magnetization region, and the magnetic sensor which applies the alternate current magnetism to the magnetic material thus performing the alternate current excitation in the direction which oscillates the direct current magnetization, and measures the alternate current magnetic field generated due to the interaction between the magnetic material and both of the direct current magnetism and the alternate current magnetism, and particularly the component of the alternate current magnetic field in the direction of the alternate current excitation. This does not exclude the structure where the magnetism which is preliminarily formed by synthesizing the direct current magnetism and the alternate current magnetism is applied to the magnetic material.

(6) In the magnetism measuring device described in (5), the magnetic sensor is configured such that an alternate current excitation coil and a detection coil are wound around one ferromagnetic core.

(7) In the magnetism measuring device described in (5), the magnetic sensor is configured such that an alternate current excitation coil and a detection coil are wound around different ferromagnetic cores, and the ferromagnetic core around which the alternate current excitation coil is wound and the ferromagnetic core around which the detection coil is wound are arranged at positions opposite to each other with the magnetic material sandwiched therebetween.

(8) In the magnetism measuring device described in (6), the magnetism measuring device includes two magnetic sensors, and the magnetic sensors are arranged at positions opposite to each other with the magnetic material sandwiched therebetween.

(9) A method of evaluating quality of a magnetic material in which, using the component of the alternate current magnetic field orthogonal to the direction of the direct current magnetization measured by the magnetism measuring method according to any one of (1) to (4), a degree of displacement of an angle of an easy axis of magnetization of crystals in the magnetic material with respect to a direct current magnetization direction is evaluated.

It is desirable that the degree of displacement of the angle of the easy axis of magnetization with respect to the direct current magnetization direction is quantitatively evaluated in terms of a quantitative index or the like.

(10) A method of evaluating quality of a magnetic material in which, using the component of the alternate current magnetic field orthogonal to the direction of the direct current magnetization measured by the magnetism measuring method according to any one of (1) to (3), a magnetic property expressed by a B8 value and/or a degree of variation in a crystal orientation of the magnetic material are obtained, and thereby quality of a magnetic material is evaluated.

(11) A method of evaluating quality of a grain-oriented electrical steel sheet in which, using the component of the alternate current magnetic field orthogonal to the direction of the direct current magnetization according to (4) measured by the magnetism measuring method, a magnetic property expressed by a B8 value and/or a degree of variation in a crystal orientation of the grain-oriented electrical steel sheet are obtained, and thereby quality of a grain-oriented electrical steel sheet is evaluated.

(12) A magnetic material evaluation device provided with a calculation means into which the component of the alternate current magnetic field orthogonal to the direction of the direct current magnetization measured by the magnetism measuring device according to any one of (5) to (8) is inputted and which calculates a degree of displacement of an angle of the easy axis of magnetization of crystals in the magnetic material with respect to the direct current magnetization direction.

It is desirable that the degree of displacement of the angle of the easy axis of magnetization with respect to the direct current magnetization direction is evaluated as a quantitatively evaluation value in terms of a quantitative index or the like.

(13) A magnetic material evaluation device provided with a calculation means into which the component of the alternate current magnetic field orthogonal to the direct current magnetization direction measured by the magnetism measuring device according to any one of (5) to (8) is inputted and which calculates a magnetic property expressed by a B8 value and/or a degree of variation in a crystal orientation of the magnetic material.

(14) A manufacturing method of a grain-oriented electrical steel sheet includes a step in which the two-dimensional distribution of the magnetic property expressed by a B8 value and/or the degree of variation in the crystal orientation of the grain-oriented electrical steel sheet on the grain-oriented electrical steel sheet is obtained using the method of evaluating quality of the grain-oriented electrical steel sheet according to (11), and the grain-oriented electrical steel sheet is classified in accordance with grades based on the two-dimensional distribution.

(15) A manufacturing method of a grain-oriented electrical steel sheet which includes the steps of: obtaining the two-dimensional distribution of the magnetic property expressed by a B8 value and/or the degree of variation in the crystal orientation of the grain-oriented electrical steel sheet on the grain-oriented electrical steel sheet using the method of evaluating quality of the grain-oriented electrical steel sheet according to (11); comparing the two-dimensional distribution and fluctuation of operation conditions of manufacturing steps; and improving the operation conditions of the manufacturing steps.

The improvement of the operation conditions includes prescribing of optimum conditions of temperatures, speeds, loads and the like, and specifying of causes of local or whole deterioration of magnetic properties or the like and the removal of these causes.

(16) A grain-oriented electrical steel sheet in which two-dimensional distribution information on a local magnetic property expressed by a B8 value and/or a local degree of variation in the crystal orientation of the grain-oriented electrical steel sheet which is calculated using the method of evaluating quality of a grain-oriented electrical steel sheet according to (11) is provided in a state where the two-dimensional distribution information is attached to the grain-oriented electrical steel sheet.

(17) A manufacturing method of a transformer using a grain-oriented electrical steel sheet in which the two-dimensional distribution of the magnetic property expressed by a B8 value and/or the degree of variation in the crystal orientation of the grain-oriented electrical steel sheet on the grain-oriented electrical steel sheet is obtained using the method of evaluating quality of the grain-oriented electrical steel sheet according to (11), and the selection or the estimation of performances of respective members used in the transformer is performed based on the two-dimensional distribution.

The magnetic material is magnetized with a direct current to the rotational magnetization region which has no domain wall motion whereby the measurement of the magnetic property is minimally influenced by disturbances or the like. Further, by performing the detection by making use of the finding that the difference in the magnetization stability in the direction orthogonal to the direct current magnetization direction is conspicuous between the sound part and the unsound part, it is possible to realize the measurement also with high sensitivity. Further, since the measurement is minimally influenced by the disturbance, the measurement on a manufacture line under severe conditions becomes possible leading to the more sophisticated quality control and quality assurance.

BRIEF DESCRIPTION OF THE DRAWINGS

FIG. 1A is a perspective view showing an application example.

FIG. 1B is a front view as viewed from a steel sheet rolling direction (steel sheet rolling direction being orthogonal to a plane of drawing) showing the application example of FIG. 1A.

FIG. 2A is a perspective view showing another application example.

FIG. 2B is a front view as viewed from a steel sheet rolling direction (steel sheet rolling direction being orthogonal to a plane of drawing) showing the application example of FIG. 2A.

FIG. 8A is a schematic view showing a method of quantitative comparison between the measurement of our method and an SST test.

FIG. 8B is a view showing a quantitative comparison between the measurement result of the example of FIG. 1 and a B8 value obtained by the SST test (axis of abscissas: widthwise location (mm), axis of ordinates: sensor output and B8 value).

DETAILED DESCRIPTION

The explanation is made hereinafter by taking an example where a degree of displacement (angular displacement) of the "easiness of magnetization=magnetization easiness" direction with respect to a rolling direction of a grain-oriented electrical steel sheet which is one of magnetic properties of a magnetic material is measured as an example.

A grain-oriented electrical steel sheet is generally manufactured such that steel having predetermined composition is formed into a steel ingot such as a slab by casting, the steel ingot is formed into a steel sheet having a predetermined thickness by a rolling step (hot rolling and cold rolling), and treatments such as secondary recrystallization annealing are applied to the steel sheet so that the grain-oriented electrical steel sheet in which crystal grains are arranged in a predetermined crystal orientation is manufactured. Further, a tension coating film, an insulation film or the like is applied to the grain-oriented electrical steel sheet when necessary. The rolling direction implies a rolling direction in the above-mentioned rolling steps, and a degree that the easy axis of magnetization of crystals is integrated into the rolling direction strongly influences qualities of the grain-oriented electrical steel sheet.

In the grain-oriented electrical steel sheet, regions where the crystal orientation: <100> orientation (easy axis of magnetization) conform to the rolling direction constitute sound parts. On the other hand, different from the sound parts, the grain-oriented electrical steel sheet also contains unsound parts where the <100> orientation does not conform to the rolling direction and is arranged more randomly. It is necessary to detect these unsound parts and to perform a quality control of the grain-oriented electrical steel sheet.

Figure 4:
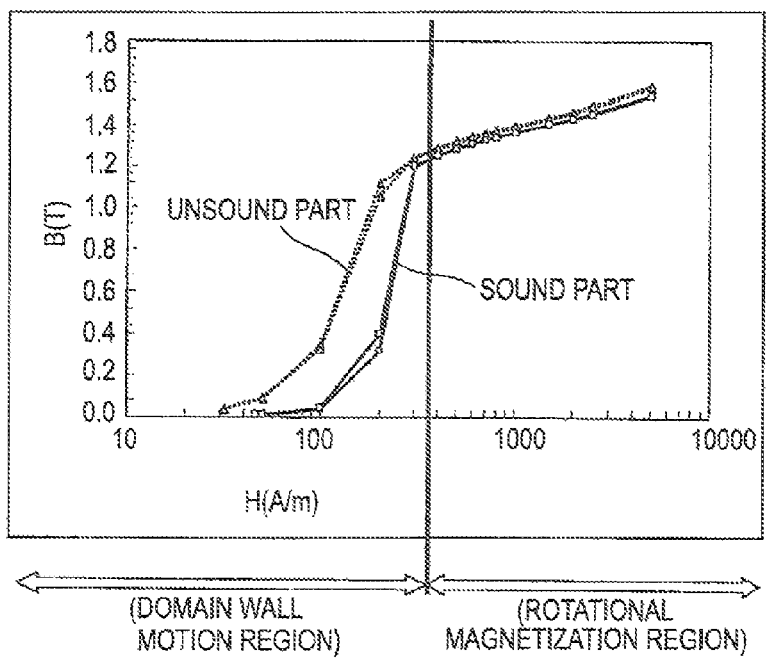
FIG. 4 is a view (B-H curve) for explaining a problem of a magnetic property measuring method.

First, the above-mentioned problem is explained by taking a magnetic property measuring method of a grain-oriented electrical steel sheet (method of detecting an unsound part of crystal orientation) as an example in conjunction with FIG. 4. FIG. 4 shows a result obtained by measuring a magnetic property (B-H curve: axis of abscissas=magnetic field strength H (unit: A/m), axis of ordinates=magnetic flux density B (unit: T)) of a sound part and an unsound part in the widthwise direction (the direction orthogonal to the rolling direction) using a single sheet tester test (SST test) device. As the magnetic property measuring method which is minimally influenced by disturbance or the like, in principle, it is thought that the measurement is performed in a rotational magnetization region by increasing the magnetization. However, the magnetic flux density B in the unsound part (indicated by white triangular mark A) and the magnetic flux density B in the sound part (indicated by white circular mark and white square mark) on the B-H curve are substantially equal in the rotational magnetization region where the external magnetic field H is large. In this manner, the large drawback in the measurement performed in the rotational magnetization region lies in that the difference in output is extremely small between the sound part and the unsound part so that sensitivity is also lowered. Accordingly, in common sense, it is determined not to be desirable to set the magnetization condition to the rotational magnetization region or more in the detection of the unsound part.

We discovered that there exists a means which substantially enhances sensitivity even in a rotational magnetization region having the above-mentioned drawback, and have arrived at our methods. The rotational magnetization region implies a magnetization region which is obtained by increasing an external magnetic field H from a zero state and by further increasing the external magnetic field H such that the external magnetic field H becomes larger than the external magnetic field H when a domain wall motion region ends. Although a boundary (a lower limit of the rotational magnetization region) falls within a region ranging from 300 to 400 A/m in the case of FIG. 4, the position of the boundary changes depending on the composition or the structure of metal. Further, at a general direct current magnetization level, two magnetization mechanisms (rotational magnetization and domain wall motion) exist in mixture and the magnetization is not limited to the situation where only one magnetization mechanism exists in a strict sense. Hence, the region where the magnetization mechanism is mainly constituted of the rotational magnetization is practically referred to as the rotational magnetization region in our methods. The rotational magnetization region may be defined as a region which has substantially no hysteresis (region where the external magnetic field H is a fixed value or more) when B-H curve data is obtained in quasi-static manner (in a quasi direct current state), for example.

Figure 5:
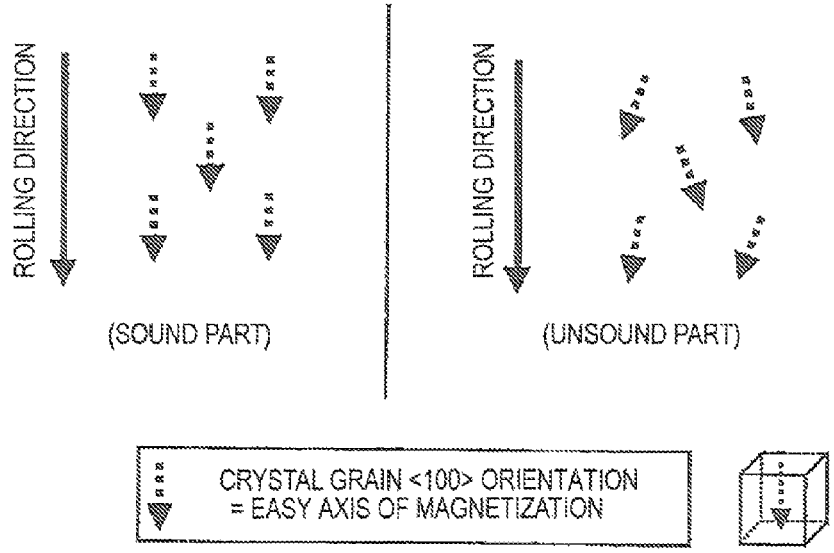
FIG. 5 is a view schematically showing a sound part where the direction of crystal grains and the rolling direction are equal and an unsound part where the orientation of crystal grains and the rolling direction are different.

FIG. 5 is a view schematically showing a mode of a sound part (left half) in which the orientation of crystal grains is equal to the rolling direction, and a mode of an unsound part (right half) in which the orientation of crystal grains is different from the rolling direction in the grain-oriented electrical steel sheet. In the grain-oriented electrical steel sheet, the unsound part and the sound part differ from each other in the orientation. In FIG. 5, the orientation of an easy axis of magnetization (<100> axis orientation) of each crystal grain is schematically indicated by a broken arrowed line. We thought that when the steel sheet is strongly magnetized in the rolling direction (indicated by a solid arrowed line) which is the easy axis of magnetization of the crystal grains in the sound part, between the sound part and the unsound part, there arises the difference in stability of magnetization (anisotropic potential energy level determined based on the crystal orientation) at the time. Then, we detected the sound part and the unsound part such that the difference in stability of magnetization between the sound part and the unsound part is detected by applying an alternate current magnetic field to the steel sheet in the direction perpendicular to the strongly magnetized rolling direction (widthwise direction) and by detecting the difference in reaction with respect to oscillations of the magnetism, that is, the difference in a generated magnetic flux.

That is, in a state where a magnetic material is magnetized with a direct current to a rotational magnetization region and an alternate current excitation is performed in a direction having a component orthogonal to a direction of the direct current magnetization, and a component of an alternate current magnetic field which is generated by an interaction between the alternate current excitation and the magnetic material in a direction orthogonal to the direction of the direct current magnetization is measured.

The alternate current excitation is performed for slightly rotating the applying direction of a magnetic field which is a resultant magnetic field formed of an alternate current magnetic field and a direct current magnetic field, that is, the vector of the applied magnetic field, from the direction of the direct current magnetic field. Accordingly, with respect to the direction of the alternate current excitation, it is sufficient that the alternate current magnetic field contains a component which is orthogonal to the direct current magnetization. The most efficient direction of the alternate current excitation is obtained when the alternate current magnetic field becomes orthogonal to the direct current magnetic field. When the alternate current magnetic field excessively departs from the orthogonal direction, the sensitivity improving effect is decreased. Hence, it is preferable to perform both the excitation and detection within 45° from the orthogonal direction.

Further, with respect to the detection direction of the alternate current magnetic field, it is necessary to investigate an amount of change in a magnetic field vector in the direction orthogonal to the direct current magnetic field. Hence, the sensor must be a sensor having sensitivity with respect to a magnetic field component in such a direction. When a magnetic sensor which exhibits a maximum value of sensitivity in the specific direction (hall element, a coil which is wound substantially on a certain plane or the like) is used, it is optimum to direct the sensitivity maximum direction toward the direction orthogonal to the direct current magnetic field. As a sensor which has a function of performing the alternate current excitation in a particular direction detecting and/or the detection of the alternate current magnetic field, a sensor which is formed by winding an excitation and/or a detection coil on a U-shaped or rod-shaped ferromagnetic core is considered. Particularly, the U-shaped sensor exhibits the excellent performance although the structure of the sensor is simple. Hence, the U-shaped sensor is suitable.

When the grain-oriented electrical steel sheet whose orientation of the crystal grains in the sound part is the rolling direction is used as an object to be measured, by magnetizing the steel sheet with a direct current to the rotational magnetization region by a direct current magnetizer and by applying an alternate current to an excitation coil of the sensor formed of a U-shaped ferromagnetic core, for example, an alternate current excitation is generated in the widthwise direction so that the magnetism is magnetically oscillated in the widthwise direction. As a result, the unsound part exhibits a larger widthwise magnetic flux change amount than the sound part. Hence, this widthwise magnetic flux change amount is detected as an electric signal by a detection coil of the sensor formed of the U-shaped ferromagnetic core. Two-dimensional scanning is performed on a steel sheet by the sensor or sensors are arranged in an array or in a staggered manner in one of the directions (for example, widthwise direction) thus acquiring the two-dimensional distribution of measured values. Then, based on the magnitudes of electric signals detected at the respective positions, the position of the sound part and the position of the unsound part can be specified. Hence, the degree of the distribution can be evaluated.

Although the direct current magnetization direction is set equal to the rolling direction, this setting is made to measure the magnetic property in the rolling direction. Our methods are not limited to such setting, and direct current magnetization direction may be suitably decided in conformity with a purpose. The technical concept lies in the constitution where the direct current magnetization direction and the alternate current excitation direction become orthogonal to each other.

Figure 6:
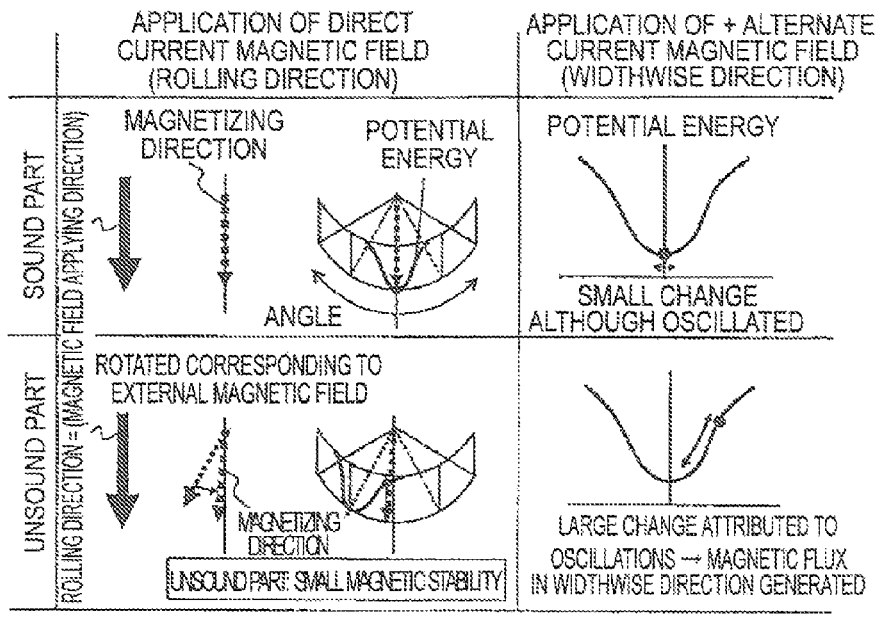
FIG. 6 is a view for schematically explaining the manner of function.

With respect to the grain-oriented electrical steel sheet whose orientation of the crystal grains in the sound part is equal to the rolling direction, the principle is explained by taking a case where the magnetic property in the rolling direction is measured as an example in conjunction with FIG. 6. FIG. 6 is a view for schematically explaining the manner of function of our methods. The drawing shows a phenomenon which occurs in a case where the direct current magnetic field is applied to the sound part (upper half) and the unsound part (lower half) respectively in the rolling direction (indicated by a bold solid line arrow) (left side), and a phenomenon which occurs in a case where the alternate current magnetic field is applied to the sound part and the unsound part respectively in the widthwise direction orthogonal to the rolling direction in addition to the above-mentioned state (right side). With respect to potential energies in the drawing, only the potential energies which are dependent on the crystal orientation are schematically depicted.

First, when the direct current magnetic field is applied to the magnetic material to the rotational magnetization region in the rolling direction, in the sound part, the easy axis of magnetization of crystals (indicated by a bold broken arrow) is equal to the magnetization direction (indicated by a broken arrow). Hence, the potential energy is held in a so-called "low state" (a state where the magnetic stability is large) (see a left upper portion of the drawing). To the contrary, in the unsound part where the easy axis of magnetization of crystals differs from the rolling direction, although the magnetic material is magnetized in the easy axis of magnetization of the respective crystal grains in a region where the intensity of the direct current magnetic field applied is low (indicated by a broken arrow: left lower portion in the drawing), when the strong direct current magnetic field which constitutes the rotational magnetization region is applied, the magnetization direction is rotated in the rolling direction which is the direct current magnetization direction (bold broken arrow: left lower portion in the drawing). Hence, a so-called state where the potential energy is elevated (a state where the magnetic stability is small) is considered to take place (see a left lower portion of the drawing).

Next, after applying the direct current magnetic field to the magnetic material, when the alternate current magnetic field is applied to the magnetic material in the widthwise direction thus magnetically oscillating the magnetic material (slightly oscillating an external magnetic field applying direction from the rolling direction), since the magnetic stability is large in the sound part, even when the steel sheet is oscillated, a change of a magnetic state is small (indicated by a both-directional fine arrow: a right upper portion in the drawing). On the other hand, since the magnetic stability is small in the unsound part, a change of a magnetic state becomes large due to oscillation (indicated by a both-directional fine arrow: a right lower portion in the drawing). The change of the magnetic state changes a magnetic field of outside of a steel sheet. Hence, the change of the magnetic state can be detected by a magnetic sensor.

To summarize the above, it is possible to realize (1) the measurement whose association with the crystal orientation is apparent (highly accurate) and (2) the measurement of the magnetic property where the magnetic material is strongly magnetized to the rotational magnetization region so that the measurement of magnetic property is hardly fluctuated by disturbance.

As can be understood from the principle shown in FIG. 6, the method is not limited to the grain-oriented electrical steel sheet, and can be broadly used for a purpose of quantifying the degree that the easy axes of magnetization of constitutional units of crystal grains or the like are arranged in the same direction (integration degree) and, further, estimating physical property which is influenced by the integration degree. Further, even when the magnetization orientations of all crystal grains are not rotated in the rolling direction due to the direct current magnetization, so long as a considerable percentage of grains are rotated, the measurement based on the principle shown in FIG. 6 is possible. Although the method also includes the measurement in a region where the rotational magnetization is dominant, the measurement in a de facto rotational magnetization region can acquire the more excellent sensitivity.

EXAMPLE 1

The explanation is made hereinafter with respect to an example where our method is applied to the measurement of a magnetic property in the rolling direction (orientation of crystal grains in the sound part being rolling direction) on a manufacture line of a grain-oriented electrical steel sheet (hereinafter simply referred to as electrical steel sheet). FIG. 1A and FIG. 1B are views showing application example 1, wherein FIG. 1A is a perspective view and FIG. 1B is a front view as viewed from a steel sheet rolling direction (steel sheet rolling direction being orthogonal to a plane of drawing). In the drawing, numeral 1 indicates an electrical steel sheet, numeral 2 indicates a direct current magnetizer, numeral 3 indicates a magnetic sensor (U-shaped sensor in this example), an arrow 4 indicates the direction of direct current magnetization, an arrow 5 indicates the direction of alternate current excitation, numeral 6 indicates an excitation coil, numeral 7 indicates a detection coil, numeral 8 indicates a ferromagnetic core, numeral 9 indicates an excitation control device, and numeral 10 indicates a signal processing device. Further, an alternate current power source and an amplifier are indicated by usual electric circuit symbols.

In FIG. 1A and FIG. 1B, the direct current magnetizer 2 and the magnetic sensor 3 are respectively arranged to face surfaces of the electrical steel sheet 1 while sandwiching the electrical steel sheet 1 which is an object to be measured therebetween. The direct current magnetizer 2 is arranged such that the direction 4 of the direct current magnetization becomes parallel to the rolling direction of the electrical steel sheet 1 (open arrow) and magnetizes the electrical steel sheet 1 with a direct current to a rotational magnetization region. A direct current electrical magnet may be arranged below a lower surface of the electrical steel sheet 1 with a liftoff of 4 mm and the magnetization is applied such that an external magnetic field H becomes 12000 A/m. In FIG. 1, the rolling direction and the direct current magnetization direction are set equal. However, the rolling direction and the direct current magnetization direction may be set opposite to each other provided that the rolling direction and the direct current magnetization direction are parallel to each other.

The direct current magnetization level is decided based on the following restriction conditions. That is,
  (i) When the direct current magnetization is excessively weak, the magnetic material becomes a region where domain wall motion occurs so that an error in measurement becomes large.
  (ii) When the direct current magnetization is excessively strong, a change of angle in the magnetization direction of a resultant magnetic field generated by the direct current magnetization and the alternate current magnetization is decreased so that sensitivity is lowered.
  (iii) When a ferromagnetic core is used as a sensor, a magnetic property of the core is changed corresponding to a level of the direct current magnetic field, and the core is magnetically saturated in an extreme case. Particularly, the core which is mounted in the inside of a magnetizer is more liable to be influenced.

Due to the above-mentioned restrictions (i) to (iii), it is desirable to perform the magnetization within a range from 800 to 16000 A/m. Although a liftoff of the direct current magnetizer may be set corresponding to an applied direct current magnetic field or the like, it is usually desirable to set the liftoff to approximately 2 to 20 mm.

As the magnetic sensor 3 which performs applying of an alternate current magnetic field and the detection of magnetic flux generated by applying of the alternate current magnetic field, a U-shaped sensor constituted by winding the excitation coil 6 and the detection coil 7 on the U-shaped ferromagnetic core 8 is used. The excitation coil 6 applies an alternate current magnetic field in a state where a level and a frequency of an applied current is controlled by the excitation control device 9. Further, an output of the detection coil 7 is inputted to the signal processing device 10, and the signal processing device 10 performs determination processing whether a measured region is a sound part or an unsound part and the degree of soundness in these parts based on intensity of the signal. In FIG. 1B, the excitation coil 6 is arranged on one leg portion of the ferromagnetic core and the detection coil 7 is arranged on other leg portion of the ferromagnetic core. However, places where the coils are arranged are not limited to the leg portions, and either one or both of coils may be arranged on a body portion of the ferromagnetic core. Further, the magnetic sensor 3 is arranged over an upper surface of the electrical steel sheet 1 with a liftoff of 2 mm such that the direction 5 of the alternate current excitation is directed in the direction orthogonal to the direction 4 of the direct current magnetization (the widthwise direction orthogonal to the rolling direction). The core 8 of the U-shaped sensor 3 is constituted by stacking electrical steel sheets, and an alternate current frequency for excitation is set to 300 Hz. It is most desirable to set the direction 5 of the alternate current excitation orthogonal to the direction 4 of the direct current magnetization. However, it is sufficient that the alternate current excitation can be performed in a state where the direction 5 of the alternate current excitation contains a component orthogonal to the direction 4 of the direct current magnetization. Accordingly, the direction 5 of the alternate current excitation may not be orthogonal to the direction 4 of the direct current magnetization in a strict sense. Although a size of the sensor 3 (open width of a U-shaped portion and a thickness in the rolling direction) may be set corresponding to a size of an investigation region unit which is a target of the measurement or a cost of the measurement, each of the minimum allowable size of the sensor is approximately 1 mm. In a case of grain-oriented electrical steel sheet, it is realistic to set the size of the sensor 3 to approximately 100 mm at maximum.

As an excitation current waveform, for example, a sinusoidal wave, a triangular wave or the like is used. The sinusoidal waveform is advantageous from a viewpoint that linear processing and a linear circuit are applicable not only on an excitation side but also on a detection side. On the other hand, with respect to the triangular waveforms, a change quantity of a generated magnetic flux per a unit time is constant between neighboring peeks of the waveform (begining from the minimum peek and ending with the maximum peek, and begining from the maximum peek and ending with the minimum peek). Accordingly, the triangular waveform has advantages such that an influence of eddy current, and a detection signal level, are held at a constant state. Although the sinusoidal wave and the triangular wave are advantageously used as described above, it is needless to say that other waveforms can be used.

Further, a signal detected by the detection coil has, when the excitation current waveform is a triangular waveform, for example, a waveform which alternately has an approximately flat portion on a plus side and a minus side. The intensity of the above-mentioned signal can be obtained in various manners. For example, an index which evaluates the intensity of the signal may be used in such a manner that an RMS value (root-mean-square value) of the whole waveform is set as the intensity of the signal or an average value of absolute values of the flat portions is set as the intensity of the signal. In data examples described hereinafter, a triangular wave is used as the excitation waveform, and an RMS value of a sampled waveform is used as the intensity of the signal.

The setting of excitation frequency may be decided based on the following restriction conditions:
  (i) Lower limit frequency: Low frequency side is determined in view of the relationship with a moving speed of an object to be measured, and it is necessary to set the lower limit frequency such that the number of excitation cycles sufficient for measurement can be ensured during a period in which the object to be measured (region to be measured) falls within a measurement range of the sensor.
  (ii) Upper limit frequency: On a high frequency side, the influence exerted by an eddy current generated in the inside of the object to be measured is increased so that a measurement error is increased. Accordingly, it is necessary to set the upper limit frequency within a range which prevents the excessive influence exerted by the eddy current.

Accordingly, although the proper excitation frequency may differ depending on various conditions, in the case of the grain-oriented electrical steel sheet, the preferable excitation frequency is set to a value which falls within a range from 100 to 10 kHz in many cases.

In the example shown in FIG. 1, the direct current magnetizer 2 is arranged below a lower surface of the steel sheet and the magnetic sensor 3 is arranged over the upper surface of the steel sheet. However, the upper surface and the lower surface may be reversed or the direct current magnetizer 2 and the magnetic sensor 3 may be arranged on the same side. Further, one set of direct current magnetizer may be arranged on both upper and lower surfaces respectively.

Figure 7:
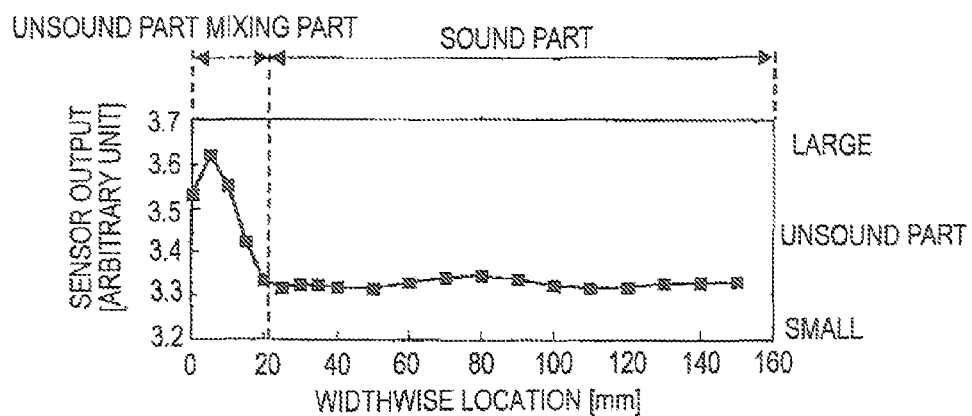
FIG. 7 is a view showing one example of a result of the measurement of the example of FIG. 1 (axis of abscissas: widthwise location (mm), axis of ordinates: sensor output).

FIG. 7 is a view showing one example of a result of the measurement according to Example 1. That is, FIG. 7 shows one example of the result obtained by applying our method to a grain-oriented electrical steel sheet (plate thickness: 0.23 mmt) which is mainly constituted of a sound part and mixes an unsound part in a portion of the sound part. As the U-shaped sensor, a sensor having an open width of 10 mm is used, and the measurement is carried out by changing a width location (axis of abscissas: unit mm). An arbitrarily unit is adopted as a sensor output (axis of ordinates). To be more specific, a signal voltage (unit V) inputted to the signal processing device 10 from the sensor is used as it is without being particularly normalized. Unless otherwise specified, this arbitrarily unit is used with respect to the sensor output hereinafter.

To compare a sensor output in a region where the sound part and the unsound part exist in mixture ranging from a width location of 0 (widthwise edge) to a location near 20 mm and a sensor output in a region of the sound part where the width location is not less than approximately 20 mm, the difference between the sound part and the unsound-part-mixing part (including a case where the whole surface is constituted of the unsound part) is clearly found. The sound part, the unsound part and the unsound-part-mixing part can be proved by the observation of a cross section of a steel sheet using an optical microscope or the like. To be more specific, when the secondary recrystallization is incomplete or is not advanced yet, it is determined that the region is the unsound-part-mixing part or the unsound part.

FIG. 8A and FIG. 8B are views showing quantitative comparison examples between Example 1 and an SST test. The SST is carried out in a test room where a cut-out specimen is used, and is used for the final performance evaluation. The SST test can perform the measurement with high accuracy. A B8 value which is a result of the SST test is one of parameters indicative of magnetic properties stipulated in JIS described in JIS C 2550 (2000) "paragraph d magnetic properties of 3 Definitions and symbols." That is, the B8 value is a value indicative of magnetic flux density B when a magnetizing force H is 800 A/m, and is a value which is generally considered to be a quantitative index of the degree of deviation (displacement) of an angle of the easy axis of magnetization with respect to the rolling direction. The magnetic property of the grain-oriented electrical steel sheet is largely influenced by such crystal orientation. Hence, the B8 value is also used as a quantitative index of magnetic property such as magnetic permeability.

Since the B8 value is a B value when H=800 A/m, the B8 value is a level which substantially corresponds to an intercept part shown in FIG. 2.17 (P. 41) of Magnetic Material Reader (edited by Motohumi Honma and Akira Higuchi, issued by Kabushiki Gaisha, Kogyo Cyosakai (1998), pp 41 and 42. Assume an angle made by the easy axis of magnetization and the excitation direction as θ, the intercept-part value becomes approximately Is·cos θ. Is is saturated magnetic flux density (a constant determined by a material). In measuring the B8 value by the SST test, the excitation is made in the rolling direction. Hence, the angular difference of the easy axis of magnetization with respect to the rolling direction may be considered as the above-mentioned θ whereby it is safe to say that the B8 value is approximately proportional to cos θ. In the actual measurement, a plurality of crystal grains which have various easy axes of magnetization exist in a measurement range. Hence, the B8 value may be considered to assume a kind of average value. However, it is safe to say that the correlation exists between the B8 value and the crystal orientation.

The correlation comparison between the B8 value and the sensor output value is carried out with respect to two kinds of grain-oriented electrical steel sheet samples. The relationship between the measurement by the sensor and the sampling position of the SST specimen (30×250 mm) is schematically shown in FIG. 8A. Further, the sensor output (arbitrary unit) obtained by this example and the B8 (T) value measured using the SST specimen are plotted on the same graph with respect to the widthwise direction for the respective grain-oriented electrical steel sheet samples, and the plotted values are shown in FIG. 8B. In these samples, a part of the unsound part is intentionally introduced. Further, measuring conditions are set substantially equal to the corresponding measuring conditions used in the case shown in FIG. 7 except for a gain of an amplifier.

It is understood that both two kinds of samples on an upper side and a lower side have favorable correlation with the sensor output (black rhombus mark and solid line in the drawing) and a B8 value which is a value of the result of the SST test (black square mark and broken line in the drawing). Since the presence of the relationship between the B8 value and the crystal orientation and the correlation between the sensor output and the B8 value described above are confirmed, the correlation between the crystal orientation and the sensor output is confirmed.

That is, the following is confirmed.

The unsound part relating to the crystal orientation can be measured.

We can realize not only the determination whether the grain-oriented electrical steel sheet is sound or unsound but also the quantitative measurement of the B8 value based on the SST test (preliminarily prepared calibration curve may be used).

Because of the nature of the B8 value as the index, it is possible to perform the quantitative evaluation of magnetic properties such as the degree of displacement of the crystal orientation, magnetic permeability and the like (for example, when the B8 value is small, it is evaluated that the degree of displacement of the crystal orientation is large. Also when the B8 value is small, it is evaluated that the level of magnetic permeability has the tendency of being lowered).

As a specific method for determining whether the grain-oriented electrical steel sheet is the sound part or the unsound part, there is a method in which an RMS value is calculated after correcting an output of the sensor (correction of sensitivity for every sensor, correction based on the measurement result of fluctuation quantity of liftoff or the like) when necessary, for example, and a measured part having the RMS value which exceeds a threshold value preliminarily determined based on the relationship between a property of an object to be measured and the sensor output is determined as a magnetically abnormal part (unsound part or unsound mixing part), and a measuring part having the RMS value which is less than the threshold value is determined as the magnetically sound part. To the contrary, in applying the measuring method, whether or not the magnetization conditions, various sizes, specifications, gaps, velocities and the like are properly set can be determined based on whether or not the difference in sensor output obtained by samples of the preliminarily prepared sound part and unsound part is not a predetermined threshold value or more, for example.

Figure 9A:
FIG. 9A is a schematic view showing an investigation method on a dead zone at an edge which is determined as a first disturbance error factor.
Figure 9B:
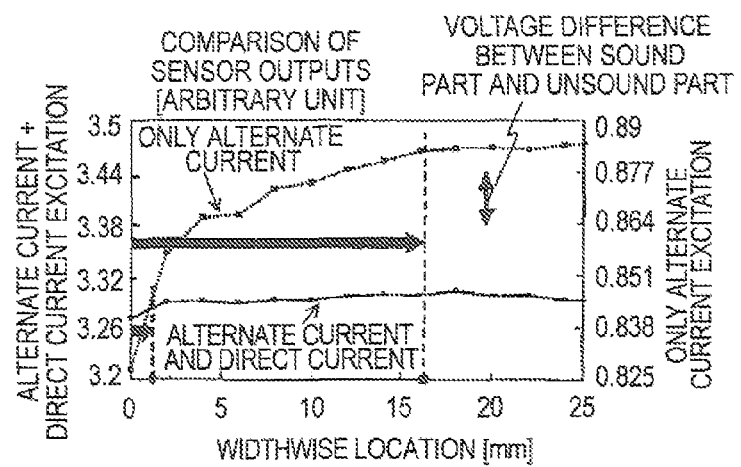
FIG. 9B is a view showing a result obtained by investigating advantageous effects of our method with respect to the dead zone at the edge which is determined as the first disturbance error factor (axis of abscissas: widthwise location (mm), axis of ordinates: sensor output).

FIG. 9A and FIG. 9B are views showing the result obtained by investigating the influence of a dead zone at an edge (defined as a first disturbance error factor) according to our method. That is, the magnitude of the dead zone at the edge of a comparison method (only alternate current excitation) and the magnitude of the dead zone at the edge of our method (alternate current excitation and direct current excitation) are compared with each other. A method which excites the steel sheet only by the alternate current excitation using the same U-shaped sensor is a magnetic measuring method which exhibits the excellent sensitivity when the region of the steel sheet is the domain wall motion region. FIG. 9A schematically shows the measuring method in accordance with both methods. That is, with respect to the sample constituted of only the sound part, the magnetism measurement is performed by moving the sensor from a widthwise edge. The measuring conditions are set substantially equal to the measuring conditions used in the case shown in FIG. 7 except for the gain of the amplifier.

FIG. 9B shows sensor outputs (arbitrary unit) obtained by the comparison method and our method which are plotted on the same graph with respect to the widthwise locations. To align the standards of outputs obtained by two measuring methods, scales on axis of ordinates are aligned such that the output difference (vertical both-arrowed mark in FIG. 9B) between the sound part and the unsound part by the respective methods becomes equal. Although a dead zone at an edge (a region where the lowering of sensor output is observed, that is, the region where the lowering of sensitivity is observed) having a width of approximately 16 mm is recognized from the edge in the widthwise direction in the comparison method, a width of the dead zone at the edge is extremely small, that is, approximately 1 mm.

Figure 10:
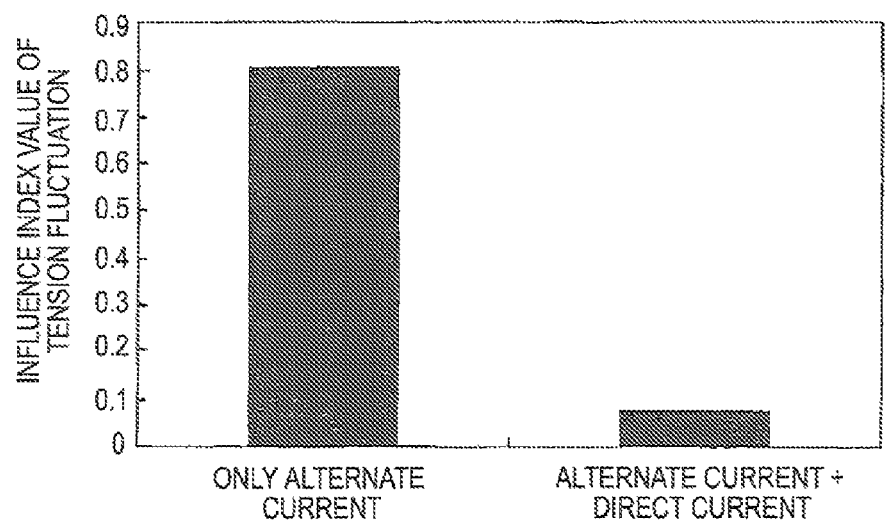
FIG. 10 is a view showing a result obtained by investigating advantageous effects of our method with respect to tension which is determined as a second disturbance error factor.

FIG. 10 is a view showing the result obtained by investigating the influence of tension (tensile strength, stress) (defined as a second disturbance error factor) according to our method. An index for evaluating the influence of the fluctuation of tension is taken on an axis of ordinates, and a case where only the alternate current excitation is used (same as the comparison method shown in FIG. 9B) and a case where the alternate current excitation and the direct current magnetization are used are compared with each other. The measuring conditions are set substantially equal to the measuring conditions used in the case shown in FIG. 7 except for the gain of the amplifier. An influence index value of the fluctuation of tension is expressed as a ratio between a change quantity $\Delta V_0$ of the sensor output (arbitrary unit) when the sound part is measured in a state where tension is changed by a unit tension change quantity (for example, 1 kgf/mm² or the like) and an absolute value $\Delta V_1$ of the difference between a sensor output of the sound part and a sensor output of the unsound part when tension of a predetermined value is applied.

Data in FIG. 10 are, to be more specific, calculated as follows:

1) An output change quantity $\Delta V_0$ of the sensor when the tension is changed from 0.8 kgf/mm² to 1.6 kgf/mm² is measured.
2) An output change quantity $\Delta V_0'$ (=1.125$\Delta V_0$) is calculated for conversion in terms of a tension change quantity of 1 kgf/mm².
3) A sensor output $V_1$ of the sound part and an output $V_2$ of the unsound part are measured at tension of 1.2 kgf/mm².
4) An index value (unit [1/(kgf/mm²)]) is calculated using a formula $\Delta V_0'/|V_1-V_2|$.

This index value is a sensor output attributed to the fluctuation of tension corresponding to the difference in sensor output between the sound part and the unsound part. Hence, this index value implies that the smaller the index value, the less the measurement is influenced by the fluctuation of tension. In FIG. 10, when only the alternate current excitation is performed (left side), the index value is close to 1. Hence, the graph implies that an output change attributed to the fluctuation of tension and an output change attributed to the difference in sensor output between the sound part and the unsound part are substantially equal. On the other hand, it is understood that, in our method which uses the alternate current excitation and the direct current magnetization (right side), the index value is not more than 0.1. Hence, it is possible to distinguish the sound part and the unsound part from each other without being influenced by the fluctuation in tension.

Figure 11:
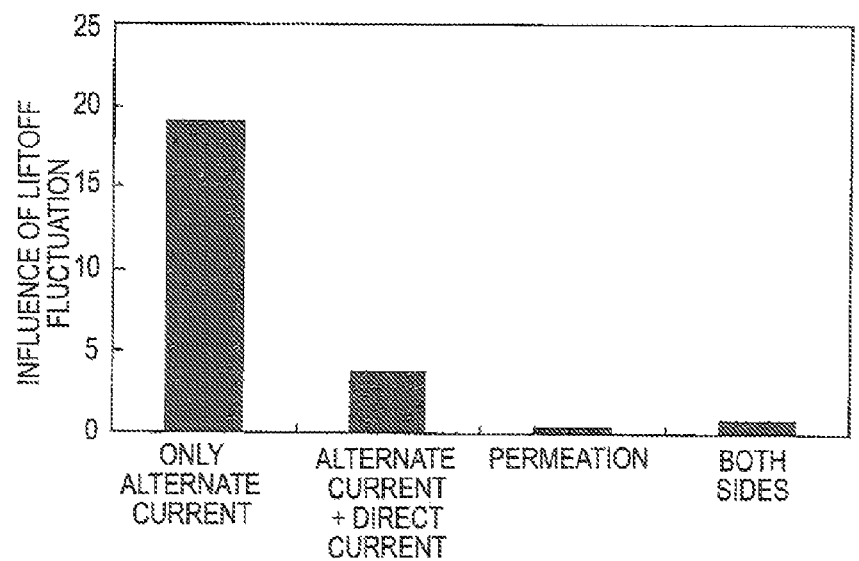
FIG. 11 is a view showing a result obtained by investigating advantageous effects of our method with respect to liftoff which is determined as a third disturbance error factor.

FIG. 11 is a view showing the result obtained by investigating the influence of liftoff (defined as a third disturbance error factor) according to our method. In the same manner as the investigation shown in FIG. 10, an index for evaluating the influence of the fluctuation of liftoff is taken on an axis of ordinates, and a case where only the alternate current excitation is used and the case where the alternate current excitation and the direct current magnetization are used are compared with each other. The measuring conditions are set substantially equal to the measuring conditions used in the case shown in FIG. 7 except for the gain of the amplifier. An influence index value of the fluctuation of liftoff is expressed as a ratio between a change quantity $\Delta V_{L0}$ of the sensor output (arbitrary unit) when the sound part is measured in a state where liftoff is changed by a unit change quantity (for example, 1 mm or the like) and an absolute value $\Delta V_{L1}$ of the difference between a sensor output of the sound part and a sensor output of the unsound part when liftoff of a predetermined value is set.

Data in FIG. 11 are, to be more specific, calculated as follows:

1) An output change quantity $\Delta V_{L0}$ of the sensor when the liftoff is changed from 1.5 mm to 2.5 mm is measured.
2) Since the liftoff fluctuation quantity is 1 mm, an output change quantity $\Delta V_{L0}'$ is set to satisfy the relationship $\Delta V_{L0}'=\Delta V_{L0}$.
3) A sensor output $VL_1$ of the sound part and an output $V_{L2}$ of the unsound part are measured at liftoff of 2 mm.
4) An index value (unit [1/mm]) is calculated using a formula $\Delta V_{L0}'/|V_{L1}-V_{L2}|$.

This index value is a sensor output attributed to the fluctuation of liftoff corresponding to the difference in sensor output between the sound part and the unsound part. Hence, this index value implies that the smaller the index value, the less the measurement is influenced by the fluctuation of liftoff. FIG. 11 shows that when only the alternate current excitation is performed (left end), the output change when the liftoff is fluctuated by 1 mm becomes extremely large compared to the output change attributed to the difference between the sound part and the unsound part. On the other hand, it is understood that, in our method which uses the alternate current excitation and the direct current magnetization (second position from the left side), the output change can be suppressed to approximately ⅕ of the output change compared to a case where only the alternate current excitation is performed. It is preferable to set an absolute value of the liftoff to approximately 0 to 50 mm. In FIG. 11, "permeation" at the third position from the left and "both sides" at the right end respectively show results of Example 2 (permeation arrangement) and Example 3 (both-sides arrangement) described later.

The alternate current magnetic sensor having the alternate current excitation part and the detection part has been explained heretofore with respect to a case where the alternate current excitation part and the detection part are arranged on the same side with respect to the object to be measured. However, to reduce the fluctuation of liftoff or the like, depending on the required specification of the alternate current magnetic sensor, two kinds of variations which are described hereinafter (Example 2 and Example 3) can be used with respect to the sensor constitution.

As has been explained heretofore, it is found that we can remarkably enhance the magnetic measurement also with respect to disturbance error factors such as the dead zone at the edge, tension or liftoff compared to the comparison method which is the magnetic measuring method exhibiting excellent sensitivity in the domain wall motion region. As the disturbance error factors other than the above-mentioned disturbance error factors, the crystal grain size or precipitates are considered. However, both crystal grain size and precipitates are resistance factors against the domain wall motion and the rotation of the magnetization direction. Hence, it is expected that the influence which these factors exert on the rotational magnetization region is small.

The explanation has been made by taking the example in which the rolling direction is set as the reference direction, and the degree of displacement of the easy axis of magnetization with respect to the rolling direction is measured. However, the reference direction is not limited to the rolling direction, and an optimum direction is suitably selected and set in conformity with an object to be measured, and a direct current magnetic field may be applied in the direction. Further, it is needless to say that our method is not limited to the measurement of the degree of displacement of the crystal orientation and is also applicable to the measurement of magnetic properties which are influenced by the degree of displacement of the crystal orientation. Although a shape of an object to be measured is not limited, our measuring method is a method suitable for a plate-shaped material (having a thickness of not more than approximately 2 mm). The measuring method is particularly suitably applicable to a line which continuously manufactures or treats a strip-shaped magnetic material. In the case of a grain-oriented electrical steel sheet, it is preferable to perform the measurement in a final quality assurance apparatus section (a section in a manufacturing line where main manufacturing processes are completed and a shape and magnetic properties of the steel sheet are evaluated as an inspection carried out before being shipped as steel strip) or the like. Further, from a viewpoint of time necessary for measurement and the like, it is preferable to use sensors which are arranged in the widthwise direction (it is more preferable to arrange the sensors in a staggered manner for obviating the physical interference between the neighboring sensors).

EXAMPLE 2

An alternate current excitation part and a detection part of a sensor are separated from each other (coils are wound around separate cores), and are arranged at positions opposite to each other with an object to be measured sandwiched therebetween (referred to as permeation arrangement). Accordingly, although a distance between a magnetic material and the alternate current excitation part and a distance between the magnetic material and the detection part may fluctuate (liftoff fluctuation), there is no change in distance between the excitation part and the detection part. That is, there is a tendency that a liftoff fluctuation quantity which is generated between the excitation part and the magnetic material and a liftoff fluctuation quantity which is generated between the detection part and the magnetic material offset each other. Hence, the influence of the liftoff fluctuation on the magnetism can be decreased.

In a manufacture line of a grain-oriented electrical steel sheet, Example 2 to which our method is applied is explained hereinafter. FIG. 2A and FIG. 2B are views showing application example 2, wherein FIG. 2A is a perspective view and FIG. 2B is a front view as viewed from a rolling direction. In the drawing, numeral 1 indicates an electrical steel sheet (object to be measured), numeral 2 indicates a direct current magnetizer, numeral 20 indicates a part of a magnetic sensor, that is, a magnetic sensor excitation part which is formed by winding an excitation coil 20*b* around an excitation ferromagnetic core 20*a*, numeral 21 indicates a part of the magnetic sensor, that is, a magnetic sensor detection part which is formed by winding a detection coil 21*b* around a detection ferromagnetic core 21*a*, an arrow 4 indicates the direction of direct current magnetization, and an arrow 5 indicates the direction of an alternate current excitation respectively (the position of the magnetic sensor excitation part 20 and the position of the magnetic sensor detection part 21 may be exchanged). Further, an alternate current power source and an amplifier are indicated by usual electric circuit symbols.

As shown in FIG. 2B, the magnetic sensor excitation part 20 is connected to an oscillation circuit and generates an alternate current magnetic field. On the other hand, the magnetic sensor detection part 21 is connected to an electronic circuit and detects a coil output. Based on a detected signal, a degree of an unsound part, a crystal orientation (a degree of alignment of <100> orientation with respect to a rolling direction), a magnetic property value (a B8 value based on an SST test) and the like are estimated. Other constitutions, preferred conditions and application modes are substantially equal to the corresponding constitutions, conditions and application modes shown in FIG. 1.

In the above-mentioned constitution, different from the constitution described above in conjunction with FIG. 1B, a sensor output becomes smaller (than sound part) in an unsound part. This is because that, in FIG. 2B, out of a magnetic flux which flows out from the excitation coil, a rate of a magnetic flux which flows as a magnetic flux A becomes large in the unsound part. Hence, a rate of a magnetic flux which flows as a magnetic flux B becomes small to the contrary (magnetic flux which is detected by the detection part).

The core of the magnetic sensor excitation part and the core of the magnetic sensor detection part are arranged to face each other in an opposed manner with a steel sheet sandwiched therebetween while aligning the arrangement directions of the legs. The specifications (core size, shape, material, coil specification and the like) of the magnetic sensor excitation part and the magnetic sensor detection part can be separately set.

Among coil specifications, various cases are conceivable with respect to winding of the coils around the core or the connection when a plurality of coils are wound. One example is shown in FIG. 2B. A plurality of coils (three coils in FIG.

2B) are used as the excitation coil and three coils are connected to an alternate current power source in series, and a plurality of coils are used as the detection coil and the respective detection coils are connected to amplifiers respectively. Both the excitation coil and the detection coil may be formed of single coil. When the excitation coil or the detection coil is formed of a plurality of coils, the coils may be connected in series partially or wholly.

Basically there arises no problem even when the position of the magnetic sensor excitation part 20 and the position of the magnetic sensor detection part 21 are exchanged. Further, with respect to the direct current magnetizer 2 (not shown in FIG. 2B), one additional set of direct current magnetizer 2 may be provided above the electrical steel sheet 1. In this case, it is necessary to arrange the magnetization direction such that the magnetization directions are directed in the same direction within a plane of an object to be measured.

Mounting of two sets of the direct current magnetizer above and below the electrical steel sheet in symmetry acquires the following advantages although the mounting has a disadvantage that the number of constitutional elements is increased so that a cost is pushed up, and so forth:

(1) The influence caused due to the fluctuation of a distance between the steel sheet and the direct current magnetizer works on the upper and lower magnetizers respectively in opposite directions (when the steel sheet is shifted away from one magnetizer, the steel sheet approaches the other magnetizer). Hence, a magnetic field applied to the steel sheet is stabilized whereby the influence of the fluctuation of liftoff exerted on the sensor output becomes small.

(2) Attraction forces of the steel sheet generated by the direct current magnetizers are also offset so that the influences such as a change in the distance between the sensor and the steel sheet due to the attraction of steel sheet to the magnetizer can be reduced.

(3) In the magnetizing the steel sheet to a fixed level, compared to a case where one set of magnetizer is used, when two sets of magnetizers are used, a magnetizing force necessary for one set of magnetizer can be approximately halved so that the magnetizer can be miniaturized whereby the reduction of weight of a head and space saving can be realized and, at the same time, a magnetizing current can be decreased thus suppressing the heat generation due to Joule's heat.

These advantageous effects can be obtained in the same manner also in a case where the second direct current magnetizer is applied to Example 1.

The electrical steel sheet 1 which is an object to be measured is magnetized with a direct current to a rotational magnetization region by the direct current magnetizer 2 such that the direction 4 of the direct current magnetization becomes equal to the rolling direction of the electrical steel sheet 1. In Example 2, the direct current electromagnet is set below the electrical steel sheet 1 with a liftoff of 7 mm, and an external magnetic field H of 12000 A/m is applied.

Figure 12:
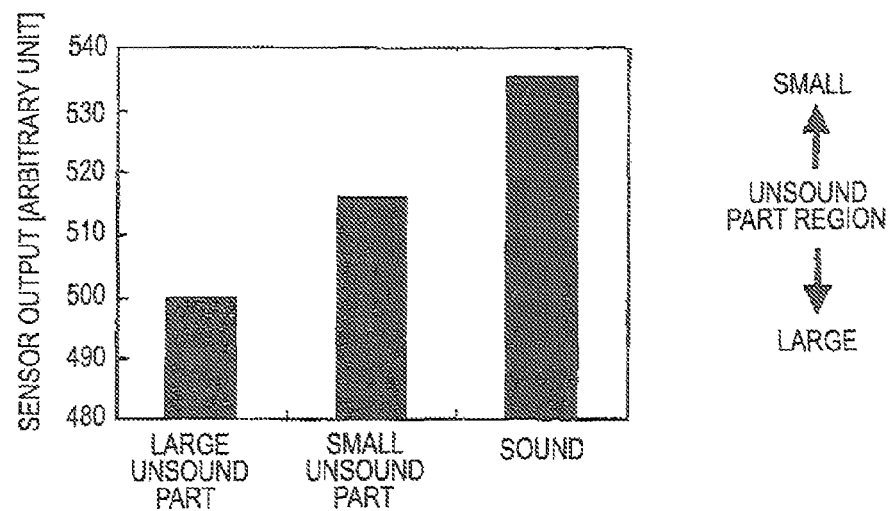
FIG. 12 is a view showing one example of a result of measurement when the example of FIG. 2 is applied to a grain-oriented electrical steel sheet.

FIG. 12 is a view showing one example of a result of a measurement when Example 2 is applied to a grain-oriented electrical steel sheet (plate thickness: 0.23 mmt). A sample which contains a large number of parts where a magnetic property such as magnetic permeability, core loss or hysteresis loss is abnormal ("large unsound parts") (left end), a sample which contains substantially only a sound part ("sound") (right end) and a sample which contains an intermediate unsound part concentration ("small unsound parts") (center) are measured with liftoffs of 5 mm of the detection part and the excitation part and at excitation frequency of 300 Hz. Other measuring conditions are set substantially equal to the corresponding measuring conditions in the case shown in FIG. 7 except for a gain of an amplifier. One direct current magnetizer 1 is used. One set of direct current magnetizer was used in the measurement. Along with the decrease of a rate of the unsound part and the increase of a rate of the sound part, a sensor output (arbitrary unit) is increased so that it is understood that a rate of the unsound part can be measured.

As can be readily understood from the influence of the fluctuation of liftoff shown in FIG. 11, it is understood that, in our device (third position from the left) in which the excitation and the detection are arranged in an opposed manner with an object to be measured sandwiched therebetween (permeation arrangement), compared to the case shown in FIG. 1B (second position from the left), the influence of the fluctuation of the liftoff is remarkably decreased. Although other property values shown in FIG. 7 to FIG. 10 are not exemplified individually here, the substantially same data are obtained.

EXAMPLE 3

With respect to the sensor having the constitution shown in FIG. 1B where one sensor includes both of the excitation part and the detection part with an object to be measured (magnetic material) sandwiched therebetween, another one set of such a sensor is arranged on an opposed side (at an opposed position) (referred to as both-sides arrangement). Accordingly, signal changes of both sensors become substantially symmetrical with respect to the change in distance between a magnetic material and the sensor (fluctuation of liftoff) so that the signal changes offset each other whereby the influence of the fluctuation of liftoff can be made small. In the same manner as "the second example", the direct current magnetizer may be mounted on one side of the object to be measured or on both sides of the object to be measured.

Figure 3A:
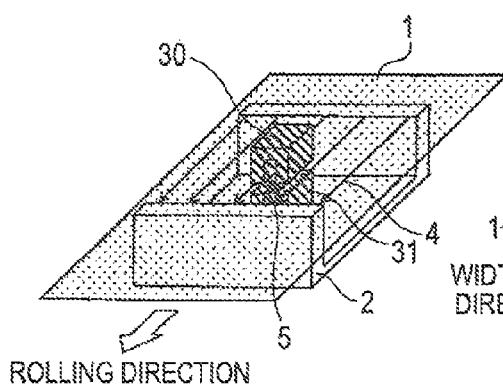
FIG. 3A is a perspective view showing yet another application example.
Figure 3B:
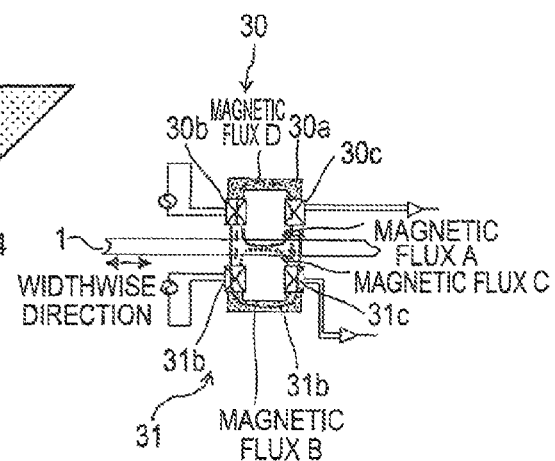
FIG. 3B is a front view as viewed from a steel sheet rolling direction (steel sheet rolling direction being orthogonal to a plane of drawing) showing the application example of FIG. 3A.

In a manufacture line of a grain-oriented electrical steel sheet, Example 3 to which our methods is applied is explained hereinafter. FIG. 3A and FIG. 3B are views showing application example 3, wherein FIG. 3A is a perspective view and FIG. 3B is a front view as viewed from a rolling direction. In the drawing, numeral 1 indicates an electrical steel sheet (object to be measured), numeral 2 indicates a direct current magnetizer, numeral 30 indicates a magnetic sensor which is formed by mounting an excitation coil 30b and a detection coil 30c on a ferromagnetic core 30a, numeral 31 indicates a magnetic sensor which is formed by mounting an excitation coil 31b and a detection coil 31c on a ferromagnetic core 31a, an arrow 4 indicates the direction of direct current magnetization, and an arrow 5 indicates the direction of an alternate current excitation respectively. Further, an alternate current power source and an amplifier are indicated by usual electric circuit symbols.

As exemplified in FIG. 3B, the excitation coils 30b, 31b are connected to an oscillation circuit and generate an alternate current magnetic field. On the other hand, the detection coils 30c, 31c are connected to an electronic circuit and detect coil outputs. Based on detected signals, a degree of an unsound part, a crystal orientation (a degree of alignment of <100> orientation with respect to a rolling direction), a magnetic property value (a B8 value based on an SST test) and the like are calculated.

Two sensors are arranged to face each other in an opposed manner with a steel sheet sandwiched therebetween while aligning the arrangement directions of the legs. The excitation directions of two excitation coils are controlled such that the flow directions of alternate current magnetic fluxes (a flux A and a flux C in FIG. 3B) in the inside of the steel sheet agree with each other. Although the specifications (core size, shape, material, coil specification and the like) of the magnetic sensors 30, 31 can be separately set, in general, the magnetic sensors 30, 31 have the same specification by emphasizing the symmetry between the magnetic sensors 30, 31.

According to this constitution, in general, in the same manner as the constitution shown in FIG. 1B explained previously, a sensor output becomes larger in an unsound part. To the measurement using the magnetic sensor 30, the magnetic flux A which returns to the same side as the excitation coil 30b by way of the object to be measured, the magnetic flux B which permeates the object to be measured, goes through the opposing magnetic sensor 31 and returns again by permeating the object to be measured, and a magnetic flux D which is generated from the excitation coil 31b of the opposing magnetic sensor 31 and permeates the object to be measured are relevant. At the position of the detection coil 30c, the direction of the magnetic flux B and the direction of the magnetic flux D are opposite to each other, and a magnetic flux level of the magnetic fluxes B and a magnetic flux level of the magnetic fluxes D are considered substantially equal. Hence, the magnetic flux B and the magnetic flux D offset each other so that the influence of the magnetic flux A becomes dominant. The same goes for the magnetic sensor 31 (the magnetic flux B and the magnetic flux D offset each other so that the influence of the magnetic flux C becomes dominant).

Among coil specifications, various cases are conceivable with respect to winding of the coils around the core or the connection when a plurality of coils are wound. One example is shown in FIG. 3B. One coil is used as the excitation coil and one coil is used as the detection coil.

The electrical steel sheet 1 which is an object to be measured is magnetized with a direct current to a rotational magnetization region by the direct current magnetizer 2 (not shown in FIG. 3B, and when one direct current magnetizer is arranged above and below the electrical steel sheet 1 respectively, two direct current magnetizers are aligned with each other so that the directions of the magnetic fields are strengthened each other) such that the direction 4 of the direct current magnetization becomes equal to the rolling direction of the electrical steel sheet 1. In Example 3, the direct current electromagnet (direct current magnetizer) is set below the electrical steel sheet 1 with a liftoff of 7 mm, and an external magnetic field H of 12000 A/m is applied.

Figure 13:
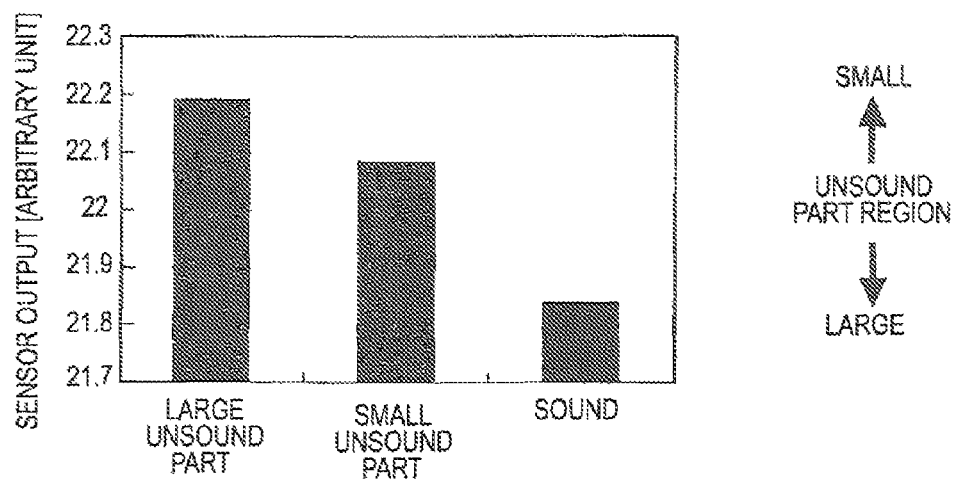
FIG. 13 is a view showing one example of a result of measurement when the example of FIG. 3 is applied to a grain-oriented electrical steel sheet.

FIG. 13 is a view showing one example of a result of a measurement when Example 3 is applied to a grain-oriented electrical steel sheet (plate thickness: 0.23 mmt). A sample which contains a large number of parts where a magnetic property such as magnetic permeability, core loss or hysteresis loss is abnormal ("large unsound parts") (left end), a sample which contains substantially only a sound part ("sound") (right end) and a sample which contains an intermediate unsound part concentration ("small unsound parts") (center) are measured with liftoffs of 4 mm from both magnetic sensors at excitation frequency of 300 Hz. Other measuring conditions are set substantially equal to the corresponding measuring conditions used in the case shown in FIG. 7 except for a gain of an amplifier. One direct current magnetizer is used. Along with the decrease of a rate of the unsound part and the increase of a rate of the sound part, a sensor output (arbitrary unit) is increased so that it is understood that a rate of the unsound part is measured.

As indicated by the influence of the fluctuation of liftoff shown in FIG. 11, it is understood that, according to our device (right end) in which the magnetic sensor formed by winding the excitation coil and the detection coil on one core is arranged on both sides of the object to be measured in a state where the magnetic sensors sandwich the object to be measured therebetween, compared to the case shown in FIG. 1B (second position from the left), the influence of the fluctuation of the liftoff is remarkably decreased. Although other property values shown in FIG. 7 to FIG. 10 are not exemplified individually here, the substantially same data are obtained.

Application Example

Our magnetic measuring method and device which have been explained heretofore can be used as a quality evaluating method and device of an electrical steel sheet on a final stage of a manufacturing process of the electrical steel sheet, for example. However, different from the conventional quality evaluation, our magnetic measuring method and device can perform, not only a function of distinguishing a sound part and an unsound part from each other (a defect detector), but also a function of performing a local online quantitative measurement of the important magnetic property referred to as the B8 value obtained by a conventional SST test based on a cut sheet. Accordingly, it is also possible to evaluate the distribution of fluctuation of the B8 values at portions of the steel sheet which are treated as the sound parts. Further, the superiority or inferiority in magnetic property or the like among the sound parts can be evaluated based on the B8 value. Also, a conveying speed of a steel sheet (steel strip) at the time of measurement is not particularly limited and the measurement can be carried out at several hundred mpm. Also, an index other than a B8 value can be used with no problem provided that the index can be correlated with the sensor output based on our measuring method due to an investigation corresponding to the investigation shown in FIG. 8A. What is important is a quantitative index value can be calculated.

Figure 14:
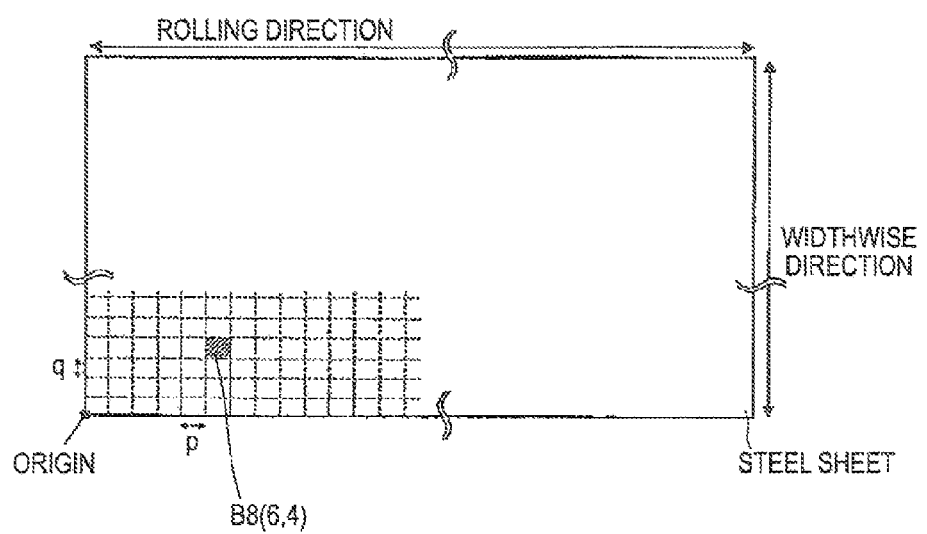
FIG. 14 is a view showing an example where quantitative measured values are indicated for every two-dimensional region on a steel sheet.

For example, as shown in FIG. 14, a surface of a steel sheet is partitioned two-dimensionally at a rolling direction pitch p[m] and a widthwise direction pitch q[m] to form regions, and locations of the respective regions are expressed as relative coordinates from a certain reference point ("origin," a widthwise direction edge of a distal end portion of a steel sheet, for example), and a quantitative measured value can be indicated for every region (a B8 value for every region in the example shown in FIG. 14). The rolling direction pitch and the widthwise direction pitch may be respectively set to a fixed value or the pitch may be set finer only at important portions in terms of control (for example, portions in the vicinity of an edge portion in the widthwise direction or in the rolling direction). For example, in the grain-oriented electrical steel sheet, the widthwise direction pitch q may preferably be set to approximately 2 to 10 mm at the edge portion in the widthwise direction. The rolling direction pitch q may be set to approximately 1 to 1000 mm.

With the use of the B8 value distribution information which is the result of the above-mentioned evaluation, it is possible to perform the finer or more precise quality evaluation than before. For example, the grading of the steel sheet can be realized. As the grading method, various grading can be used also corresponding to shipping modes such as a steel sheet (including a cut sheet strip) or a plate. For example, the grading may be performed as follows:

A grade: B8 value being not less than 1.92 T in a two-dimensional region covering not less than 95% of a surface of a steel sheet B grade: B8 value being not less than 1.90 T in a two-dimensional region covering not less than 95% of a surface of a steel sheet C grade: B8 value being not less than 1.88 T in a two-dimensional region covering not less than 95% of a surface of a steel sheet.

Further, the grading may also be performed together with a value measured by quality control equipment other than our device, wherein such a value may be an evaluation value such as a core loss, for example. The grading may be also performed by using a lowest value of B8 value and setting the evaluation reference such as "the lowest value of the B8 value on the steel sheet is not less than **T."

Due to such grading of steel sheets, also in a maker which manufactures transformers from an electrical steel sheet, it is possible to easily control (or guarantee) quality of transformers with more precision. For example, in dividing the steel sheet into transformer parts having a small size using the B8 value distribution information, by selecting the transformer parts after grasping properties of respective transformer parts and by using the transformer parts corresponding to the grade of the transformer, it is possible to enhance quality precision of the transformer. Further, different kinds of transformers can be also manufactured efficiently with high accuracy. Even when the transformer is manufactured without selecting the parts, it is possible to perform grading by estimating the quality of the obtained each transformer with high accuracy based on magnetic property data of the partial steel sheet.

Further, apart from the above, the magnetic measuring method and the estimating method are also useful in stabilizing manufacturing conditions of the grain-oriented electrical steel sheet as described below. For example, assume a case where, also in the sound part, a relative fluctuation pattern of a B8 value (fluctuation tendency of property in the widthwise direction: for example, slightly lower B8 values generated only one side edge, cyclic fluctuation of the rolling direction, or the like) occurs. In this case, by analyzing the pattern using the measuring method, or the like, it is possible to specify a manufacturing step by which the fluctuation occurs in the process up to the measurement, and to reflect the result of the pattern analysis to the improvement of operational conditions of the step.

In the manufacture of the grain-oriented steel sheet, to realize the excellent magnetic property of a final product, it is necessary to control operational conditions with extreme high accuracy in many steps from a stage of slab such as hot rolling, cold rolling, annealing, film coating and the like. There may be a case where the fluctuation of an operational condition in an intermediate step (for example, temperature variation at the time of cooling or heating, temperature variation generated by a contact of the steel sheet with a holding part at the time of conveyance) appears as the variation in B8 value in a final product stage.

As an example, the above-mentioned temperature variation is exemplified. In a grain-oriented electrical steel sheet, to generate a specific crystal orientation called a Goss orientation in a steel sheet finally, the steel sheet is sequentially treated through thermal, mechanical or chemical processes in multiple stages by controlling crystal orientations, grain sizes and the like. In such treatment, conditions of the manufacturing process change for every location (position in a steel strip). Hence, there may be a case where variation (non-uniformity with respect to a location) occurs in grain size distribution, crystal orientation distribution or the like in an intermediate step. As a result, there may be a case where, even in a final product, such variation appears as variation (non-uniformity with respect to a location) on magnetic property.

To be more specific, magnetic property variation which occurs in a steel sheet after completion of manufacture occurs due to one or a plurality of variations which occur during a manufacturing process consisting of temperature variation in the widthwise direction at the time of performing hot finish rolling, heating temperature variation at the time of performing annealing, cooling temperature variation at the time of performing cooling with water. For example, with respect to the temperature at the time of performing hot finish rolling, by comparing a general pattern (temperature at a widthwise edge portion being lower than a temperature at a center portion) or a result obtained by measuring a temperature of a material to be measured by a sensor (for example, two-dimensional temperature distribution measured by a radiation thermometer, or the like) with the magnetic property, it is possible to grasp and control whether or not the final magnetic property variation is relevant to temperature variation at the time of hot finish rolling.

By comparing the temperature variation, the content variation or the like which is likely to be generated in each process with the magnetic property variation, it is possible to specify or narrow down the process which becomes a cause of the magnetic property variation. Conventionally, an extremely small part of the steel sheet is cut away and is sampled as a cut sheet, and the magnetic property of the cut sheet is measured off line. Or, alternatively, a total length of the cut sheet is measured on line, which allows only the acquisition of a widthwise average value of the magnetic property. Therefore, the two-dimensional distribution of magnetic property variation cannot be obtained. Hence, the above-mentioned manufacture improvement action cannot be taken. The manufacture improvement action can be only realized by our methods for the first time.

Further, by performing the measurement two-dimensionally using the above-mentioned magnetic measuring method and device, it is possible to provide the quantitative two-dimensional distribution information on a steel sheet such as a B8 value and/or a crystal orientation together with a product. Hence, the selection or estimation of performances of respective parts used in an electric part such as a transformer can be performed.

This brings large merits to a part manufacture maker which uses electrical steel sheet. That is, with the use of the above-mentioned grain-oriented electrical steel sheet attached with information, it is possible to impart high performance to an electric part such as a transformer due to the selection and the use of a high quality part. Further, the variation on performance can be reduced by the selective use of parts. Hence, it is possible to provide a high-quality electric part. With the use of parts whose property is sufficiently known, it is possible to estimate the performance of the electric part with high accuracy. Hence, a system which uses such an electric part can be easily designed and manufactured.

As a mode in which the above-mentioned information is provided to a next step, a client or the like as data in a form of attachment, various modes can be considered. Although a mode is not particularly limited, the following modes can be considered as specific modes: (1) A mode in which the information is printed out on papers, (2) a mode in which the information is electrified and recorded in a recording medium such as an IC tag or a magnetic disc, and the recording medium is provided, and (3) A mode in which electronic information is transmitted through the internet or the like.

Industrial Applicability

It is possible to realize the magnetic property measurement and evaluation which can remarkably reduce the influence of an edge effect and other disturbance factors and realize the measurement even on a manufacture line. This measurement is applicable to not only the defect detection but also evaluation of quality, the measurement of two-dimensional distribution and the attachment of information.

Particularly, when our device is applied to the online measurement of the grain-oriented electrical steel sheet, it is useful to find and control an unsound part. Further, quality of a steel sheet can be evaluated wholly or two-dimensionally. Hence, our method contributes to the improvement of the manufacturing step, and the quality control and the quality improvement of an electrical steel sheet using part such as a transformer by a user.

Explanation of Symbols 1: electrical steel sheet
2: direct current magnetizer
3: magnetic sensor
4: direction of direct current magnetization
5: direction of alternate current excitation
6: excitation coil
7: detection coil
8: ferromagnetic core
9: excitation control device
10: signal processing device
20: magnetic sensor excitation part (permeation arrangement)
20a: excitation ferromagnetic core
20b: excitation coil
21: magnetic sensor detection part (permeation arrangement)
21a: detection ferromagnetic core
21b: detection coil
30: magnetic sensor (both-sides arrangement)
30a: ferromagnetic core
30b: excitation coil
30c: detection coil
31: magnetic sensor (both-sides arrangement)
31a: ferromagnetic core
31b: excitation coil
31c: detection coil
p: rolling direction pitch
q: widthwise direction pitch

The invention claimed is:

1. A method of evaluating quality of a magnetic material in which, using the component of the alternate current magnetic field orthogonal to the direction of the direct current magnetization measured by the magnetism measuring method comprising:
   magnetizing a magnetic material with a direct current to a rotational magnetization region;
   performing an alternate current excitation in a direction having a component orthogonal to a direction of the direct current magnetization: and
   measuring a component of an alternate current magnetic field generated by an interaction with the magnetic material in a direction orthogonal to the direction of the direct current magnetization,
   the method of evaluating quality of magnetic material comprising evaluating a degree of displacement of an angle of an easy axis of magnetization of crystals in the magnetic. material with respect to a direct current magnetization direction.

2. The method according to claim 1, wherein the component of the alternate current magnetic field in the direction orthogonal to the direction of the direct current magnetization is measured on a side opposite to a side where the alternate current excitation is performed with the magnetic material sandwiched therebetween.

3. The method according to claim 1, wherein the alternate current excitation is performed at opposing positions on both sides which face each other with the magnetic material sandwiched between both opposing positions, and the component of the alternate current magnetic field in the direction orthogonal to the direction of the direct current magnetization is measured at both opposing positions respectively with an object to be measured sandwiched between the both opposition positions.

4. The method according to claim 1, wherein the magnetic material is a grain-oriented electrical steel sheet, and the direction of direct current magnetization is a rolling direction.

5. The method of evaluating quality of a magnetic material according to claim 1, comprising obtaining a magnetic property expressed by a B8 value and/or a degree of variation in a crystal orientation of the magnetic material, and thereby evaluating quality of the magnetic material.

6. The method according to claim 4, comprising obtaining a magnetic property expressed by a B8 value and/or a degree of variation in a crystal orientation of the grain-oriented electrical steel sheet, and thereby evaluating quality of a grain-oriented electrical steel sheet.

7. A manufacturing method of a grain-oriented electrical steel sheet comprising: a step in which the two-dimensional distribution of the magnetic property expressed by a B8 value and/or the degree of variation in the crystal orientation of the grain-oriented electrical steel sheet on the grain-oriented electrical steel sheet is obtained using the method of evaluating quality of the grain-oriented electrical steel sheet according to claim 6, and the grain-oriented electrical steel sheet is classified in accordance with grades based on the two-dimensional distribution.

8. A manufacturing method of a grain-oriented electrical steel sheet comprising the steps of: obtaining the two-dimensional distribution of the magnetic property expressed by a B8 value and/or the degree of variation in the crystal orientation of the grain-oriented electrical steel sheet on the grain-oriented electrical steel sheet using the method of evaluating quality of the grain-oriented electrical steel sheet according to claim 6; comparing the two-dimensional distribution and fluctuation of operation conditions of manufacturing steps; and improving the operation conditions of the manufacturing steps.

9. A grain-oriented electrical steel sheet in which two-dimensional distribution information on a local magnetic property expressed by a B8 value and/or a local degree of variation in the crystal orientation of the grain-oriented electrical steel sheet which is calculated using the method of evaluating quality of a grain-oriented electrical steer sheet according to claim 6 is provided in a state where the two-dimensional distribution information is attached to the grain-oriented electrical steel sheet.

10. A manufacturing method of a transformer using a grain-oriented electrical steel sheet in which the two-dimensional distribution of the magnetic property expressed by a B8 value and/or the degree of variation in the crystal orientation of the grain-oriented electrical steel sheet on the grain-oriented electrical steel sheet is obtained using the method of evaluating quality of the grain-oriented electrical steel sheet according to claim 6, and the selection or the estimation of performances of respective grain-oriented electrical steel sheets used in the transformer is performed based on the two-dimensional distribution.

11. A magnetic material evaluation device provided with a calculation means into which the component of the alternate current magnetic field orthogonal to the direction of the direct current magnetization measured by the magnetism measuring device comprising:
   a direct current magnetizer which magnetizes a magnetic material with a direct current to a rotational magnetization region: and
   a magnetic sensor which performs alternate current excitation in a direction having a component orthogonal to a direction of the direct current magnetization, and measures the component of an alternate current magnetic field generated by an interaction with the magnetic material in the direction orthogonal to the direction of the direct current magnetization is inputted and which calculates a degree of displacement of an angle of the easy axis of magnetization of crystals in the magnetic material with respect to the direct current magnetization direction.

12. The device according to claim 11, wherein the magnetic sensor is configured such that an alternate current excitation coil and a detection coil are wound around one ferromagnetic core.

13. The device according to claim 11, wherein the magnetic sensor is configured such that an alternate current excitation coil and a detection coil are wound around different ferromagnetic cores, and the ferromagnetic core around which the alternate current excitation coil is wound and the ferromagnetic core around which the detection coil is wound are arranged at positions opposite each other with the magnetic material sandwiched therebetween.

14. The device according to claim 11, further comprising two magnetic sensors arranged at positions opposite to each other with the magnetic material sandwiched therebetween.

15. The magnetic material evaluation device according to claim 11 which calculates a magnetic property expressed by a $B8$ value and/or a degree of variation in a crystal orientation of the magnetic material.

* * * * *